(12) United States Patent
Saffer (10) Patent No.: US 7,543,986 B2
(45) Date of Patent: Jun. 9, 2009

(54) EQUILIBRATED C-ARM X-RAY DEVICE

(75) Inventor: Edmund Saffer, Eggolsheim (DE)

(73) Assignee: Siemens Aktiengesellschaft, Munich (DE)

( * ) Notice: Subject to any disclaimer, the term of this patent is extended or adjusted under 35 U.S.C. 154(b) by 28 days.

(21) Appl. No.: 10/592,198

(22) PCT Filed: Feb. 17, 2005

(86) PCT No.: PCT/EP2005/050713

§ 371 (c)(1),
(2), (4) Date: Jul. 9, 2007

(87) PCT Pub. No.: WO2005/084549

PCT Pub. Date: Sep. 15, 2005

(65) Prior Publication Data

US 2007/0280426 A1 Dec. 6, 2007

(30) Foreign Application Priority Data

Mar. 9, 2004 (DE) .................... 10 2004 011 460

(51) Int. Cl.
*H05G 1/02* (2006.01)
(52) U.S. Cl. .................... 378/197; 378/196; 378/198
(58) Field of Classification Search ................ 378/196, 378/197, 198
See application file for complete search history.

(56) References Cited

U.S. PATENT DOCUMENTS

| | | | |
|---|---|---|---|
| 3,281,598 A | | 10/1966 | Hollstein et al. |
| 3,892,967 A | | 7/1975 | Grady et al. |
| 4,955,046 A | | 9/1990 | Siczek et al. |
| 4,961,214 A | | 10/1990 | Van Endschot et al. |
| 5,040,203 A | * | 8/1991 | Janssen et al. .............. 378/197 |
| 5,050,204 A | * | 9/1991 | Siczek et al. ................ 378/197 |
| 5,325,413 A | | 6/1994 | Habraken et al. |
| 5,570,770 A | * | 11/1996 | Baaten et al. ............... 192/147 |
| 5,835,557 A | * | 11/1998 | Malmstrom ................. 378/197 |
| 5,912,943 A | * | 6/1999 | Deucher et al. ............ 378/98.8 |
| 6,142,667 A | | 11/2000 | Pattee |
| 6,789,941 B1 | * | 9/2004 | Grady ........................ 378/197 |

FOREIGN PATENT DOCUMENTS

| | | |
|---|---|---|
| EP | 0 350 996 | 1/1990 |
| EP | 0 539 626 | 5/1993 |

* cited by examiner

*Primary Examiner*—Allen C. Ho
(74) *Attorney, Agent, or Firm*—Schiff Hardin LLP (57) ABSTRACT

An x-ray C-arm device has a C-arm rotatable around an orbital axis proceeding perpendicular to the plane of the C-arm. The C-arm carries an x-ray source and a radiation detector, and the overall center of gravity of the C-arm and the components carried thereby exerts a first torque on the C-arm. A counterbalancing device generates a second torque that at least partially compensates the first torque. The counterbalancing device includes a counterweight that is displaceably coupled to the C-arm by a gearing arrangement.

8 Claims, 6 Drawing Sheets

EQUILIBRATED C-ARM X-RAY DEVICE

BACKGROUND OF THE INVENTION

1. Field of the Invention

The invention concerns a C-arm apparatus.

2. Description of the Prior Art

C-arm apparatuses are prevalent today in medical technology. A diagnosis or treatment device is mounted on a C-shaped base body. Due to its shape, the C-arm (and with it the diagnosis or treatment device) can move orbitally around a point of a patient to be examined or treated in order to reach various angle positions between patient and diagnosis or treatment device without having to reposition the patient.

X-ray devices in which an x-ray source is mounted at one end of the C-arm and an x-ray receiver or image intensifier is mounted at the opposite end are prevalent as diagnosis apparatuses. Such an x-ray C-arm exhibits a not-insignificant dead weight.

If it is ensured in a C-arm apparatus that, given orbital travel, the diagnosis or treatment device is aligned on the same point at every angle position, this is known as an isocentric C-arm apparatus. Most notably in x-ray C-arms designed in such a way, in which the central ray of the x-ray system proceeds through the isocenter of the arrangement situated on the orbital axis (rotation axis of the orbital motion), the overall center of gravity of the arrangement naturally lies outside of the isocenter (thus radially removed from the orbital axis) due to the weight ratios. The dead weight of the overall arrangement therefore effects a torque on the C-arm. The center of gravity of the arrangement namely gravitates towards its stable equilibrium position, thus the lowest point below the orbital axis that can be reached via the orbital movement.

Force must thus be applied counter to the intrinsic angular momentum to hold the C-arm in a specific position or given movement. For example, the C-arm must be fixed in a specific position via a suitable braking device at the support device.

However, it is desirable to achieve a weight compensation at the C-arm such that the C-arm is free of force at every travel position, meaning that no torque whatsoever relative to the rotation axis acts on the C-arm. A number of approaches have previously been pursued in order to effect a weight compensation.

A first approach is to place the x-ray source and the image intensifier such that the overall center of gravity of C-arm and x-ray device lies on the rotation axis. Due to the heavy x-ray components, as compensation for the weight of the C-arm these must be further offset towards its ends. The central ray of the x-ray system then no longer proceeds through the isocenter of the arrangement, which requires a continuous re-placement of the patient region or of the entire patient to be treated by movement of the C-arm.

In a second approach the x-ray system is placed such that its central ray passes through the isocenter. Supplementary weights are additionally attached at the C-arm ends in order to again displace the overall center of gravity of the arrangement into the isocenter. However, the heavy supplementary weights significantly increase the total weight of the arrangement and mechanically load the C-arm such that it exhibits an inherent deformation.

A third approach is to act on the C-arm with brakes and an electrical motor drive such that the torque generated by gravity from the center of gravity of the C-arm is compensated by the electrical drive and the brakes. However, it is hereby a disadvantage that the C-arm requires electrical current for movement. Given a power failure a dangerous situation for the patient could occur since, for example, no access space to said patient can be achieved by movement of the C-arm.

SUMMARY OF THE INVENTION

An object of the present invention is to provide a C-arm apparatus in which the equilibration is improved.

The object is achieved by a C-arm apparatus, in particular an x-ray C-arm apparatus, with a C-arm that can move around an orbital axis proceeding perpendicular to the C-arm plane. Auxiliary components, in particular an x-ray system including an x-ray source and an image intensifier, are mounted on the C-arm. The overall center of gravity of C-arm and auxiliary components exerts a first torque on the C-arm. The C-arm apparatus includes a compensation device for generation of a second torque that at least partially compensates the first torque. The compensation device includes a counterweight that is displaceably coupled with the C-arm via a gearing arrangement.

Due to the at least partial compensation of the first torque by the second torque, a smaller overall torque generated by gravity acts on the C-arm. Less force is thereby necessary for orbital movement of the C-arm and less retention force via a brake is necessary to secure the C-arm in a specific position. The C-arm is inherently stable (thus weight-compensated) in rotational positions in which first torque and second torque are equal and opposite. For example, a base position can be defined to which the C-arm returns due to gravity as long as no external force is exerted on it, for example with a brake arresting the C-arm is released. If the second torque counteracts the first torque insofar as that the remaining torques are only slight, the C-arm can be effortlessly moved by hand. The contrary torque (second torque) is that generated solely by gravitation acting on the counterweight. No energy feed whatsoever to the C-arm apparatus is thus necessary for the weight compensation. In particular a motor drive for weight compensation at the C-arm is not necessary; the C-arm can thus be moved without power. To increase the operating comfort a motor drive can naturally be provided on the C-arm, such a motor drive, for example, acting on said C-arm in a frictionally-engaged manner but which does not limit the operability of the C-arm given a power failure since it can be brought out of engagement without impairing the movement capability of the C-arm. The compensation device including the counterweight is not mounted on the C-arm itself, which is why the C-arm's own weight is not increased. The masses to be moved given an orbital travel of the C-arm thus remain as small as possible. A wide range of mechanical embodiments in the form of levers, gearings, cable pulls or shafts that allow a transfer or torques are possible for the compensation device or the movement coupling between counterweight and C-arm.

In a preferred embodiment of the invention the counterweight is supported such that it can rotate around a rotation axis so that an angle change at the C-arm effects the same angle change at the counterweight. Due to the orbital path of the overall center of gravity of C-arm and auxiliary components around the orbital axis, the intrinsic angular momentum of the C-arm possesses a torque likewise cosine-dependent on its rotation angle. If the counterweight can likewise rotate around a rotation axis, this thus generates a torque that is likewise cosine-dependent on its rotation angle. If the movement coupling between counterweight and C-arm is not executed in a ratio of 1:1, meaning that an angle change at the C-arm effects the same angle change on the counterweight, the cosine-dependencies of both torques are the same. It can thus be achieved that the second torque exerted on the C-arm is always equal in magnitude to the first in the opposite direction; the C-arm is thus weight compensated in every orbital position, i.e. completely weight compensated. Due to the 1:1 translation no variable lifting arms are necessary for this at the counterweight; the construction is simplified. The C-arm is free of forces at every orbital position. A fixing brake for secure arresting of the C-arm must exert only slight force. A slight friction force (for example in the gearing arrangement) on the C-arm or on the counterweight is sufficient that the C-arm stably remains at each position even without additional braking.

If the counterweight can be moved in the orbital plane (C-arm plane) of the C-arm, a space-saving design of the overall system can be achieved that barely requires an overhang laterally outside of the orbital plane. The mechanical force transfer between the counterweight and C-arm can occur in a simple manner since no angular deflection is required between the movement of the C-arm and that of the counterweight.

In a further embodiment of the invention the C-arm can be moved around an angulation axis intersecting the orbital axis at right angles. Due to its overall center of gravity, a further torque caused by gravity acts on the C-arm relative to the angulation axis via this additional degree of freedom for the C-arm movement and the auxiliary components. This can also be compensated by the compensation device and the counterweight. This causes the C-arm also to be completely weight-compensated with regard to its angulation axis or to return at least in part to a base position with inherent stability, from which base position it can be moved again with a slight displacement force. The angular weight compensation can be achieved by rotation of C-arm and counterweight in the same or opposite direction around the angulation axis.

In addition to the orbital weight compensation, the angular weight compensation is particularly simple to realize when the C-arm is movably supported on a support device that includes the compensation device. If the compensation device is introduced directly onto or into the support device, short paths for force transfer and thus a smaller designed space of the overall system result. Given a design that is rigid relative to the angulation axis, the counterweight is, for example, automatically panned as well when the C-arm is panned. A separate mechanism for the angular weight compensation is still not necessary once. Various degrees, up to the complete weight compensation can be realized by suitable dimensioning of the mass and the movement path of the counterweight or its distances relative to the angular rotation axis and orbital rotation axis.

The support device can include the compensation device with a housing. The compensation device and support device can thus be accommodated in a housing together with the counterweight. A compact C-arm apparatus thus is achieved with a gearing arrangement that is protected from dust, can emit no detritus and allows a simple cleaning and disinfection of the entire C-arm apparatus in a sterile region, for example the treatment room of a hospital. The moving parts of the C-arm are protected from contact via the housing, to the risk of damage to the operating personnel is significantly limited.

The C-arm and counterweight can be coupled via a multistage gearwheel gearing arrangement mounted on the support device and including components arranged parallel to the orbital plane. The moment translation between the overall center of gravity and counterweight is 1:1. A gearwheel gearing arrangement is designed mechanically very simple and robust. Via the gearwheels, pinions or other gearing arrangement parts arranged in parallel, a planar design of the gearing arrangement is possible relative to the orbital plane. The 1:1 translation is easily achievable due to the multi-stage nature of the gearwheel gearing arrangement and various increases or decreases of gear ratio, so a degree of freedom with regard to mass and lever arm of the counterweight arises given an at least two-stage gearwheel gearing arrangement. For example, for weight reduction of the overall system the counterweight can thus amount to half of the total mass of C-arm and auxiliary components, but act with a lever arm that is twice as long as the lever arm with which the total mass acts on the orbital axis. The torques also then completely cancel each other.

The gearing arrangement is particularly space-saving the output part of the gearwheel gearing arrangement is an extension arm having an end at which the counterweight is mounted and that exhibits an internal gearing. A nesting of the gearing arrangement and thus the smallest possible design space can be achieved via the internal gearing. Given a level gearing arrangement created by the extension arm, a fine adjustment of the second torque is possible by, for example, a fine adjustment of the length of the extension arm and therewith of the lever arm for the counterweight. The second torque thus can be adjusted such that it is exactly, oppositely equal to the first torque. Should components be exchanged during the lifespan of the C-arm apparatus, the second moment can be adapted to the new weight ratios in the system.

In a further embodiment of the invention, the gearing arrangement and counterweight include a cavity in which is arranged a cable drum for accommodation of a supply cable for the C-arm. The weight compensation and the cabling of the C-arm (thus of all moving parts, connection cables, hoses etc. of the C-arm) are thus inaccessible from the outside. Hooking or twisting of moving parts in the surroundings of the C-arm thus is prevented. The risk of injury by moving parts is minimized for operating personnel.

DESCRIPTION OF THE PREFERRED EMBODIMENTS

Figure 1:
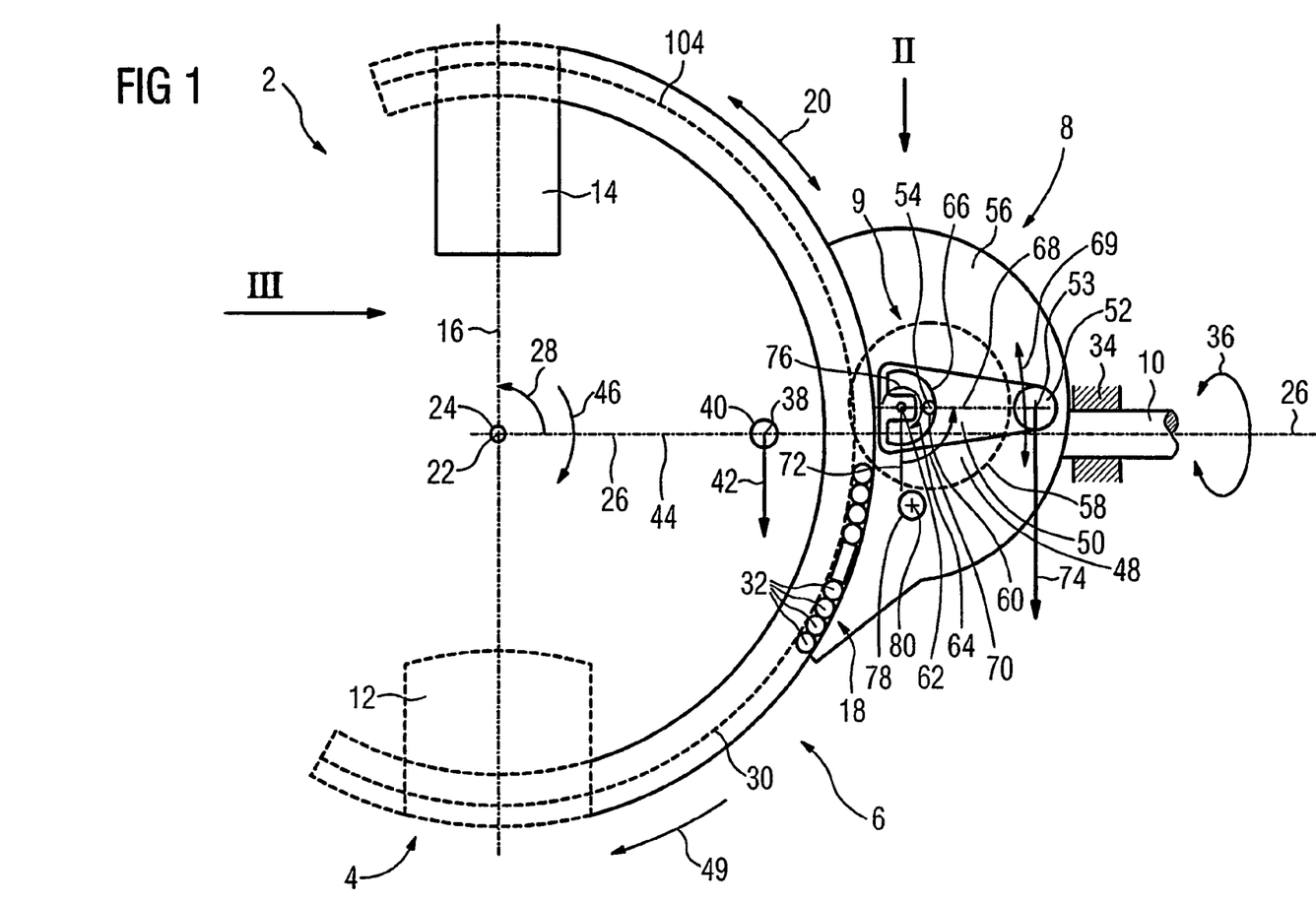
FIG. 1 is a side view of an x-ray C-arm with weight compensation in 90° orbital position and 0° angular position.

FIG. 1 shows an x-ray C-arm apparatus 2 having a C-arm 6 supporting the x-ray system 4 and a support device 8 for the C-arm 6. A portion of the stand 34 of the C-arm apparatus 2 supporting the overall arrangement on an axle 10 shown.

The x-ray system 4 has an x-ray source 12 and an x-ray receiver or image intensifier 14. The central ray 16 of an x-ray cone (not shown) emitted by the x-ray source 12 centrally leaves the x-ray source 12 and centrally strikes the image intensifier 14.

The C-arm 6 is supported such that it can move orbitally on a roller bearing 18 which is attached in a fixed manner at the support device 8. The movement direction of the C-arm 6 on the support device 8 is represented by the double arrow 20. Given such a movement C-arm 6 and x-ray system 4 describe orbital movements around an orbital axis 22 perpendicularly piercing the plane of the drawing in FIG. 1. Orbital axis 22 and central ray 16 intersect in the isocenter 24. In FIG. 1 the C-arm 6 is situated in the 90° position, meaning that the central ray 16 encompasses an angle 28 of 90° with an angulation axis 26 running horizontally and passing centrally through the bearing axle 10. Given travel in the direction 20 the C-arm 6 slides along on the rollers 32 of the roller bearing 18 on an orbital contact surface 30 attached to the C-arm 6.

In addition to the orbital movement of the C-arm 6 relative to the support device 8, C-arm 6, support device 8 and the axle 10 attached thereon can be panned around the angulation axis 26 in the direction of the arrow 36 in a journal bearing belonging to the stand (not shown) of the C-arm apparatus 2. In any orbital and angular panning position of the C-arm apparatus 2, orbital axis 22 and central ray 16 intersect at right angles and penetrate the isocenter 24 (which is stationary) as long as the stand foot of the C-arm 2 is stationary.

The total mass of C-arm 6 and x-ray system 4 at its overall center of gravity 38 is symbolically represented as a virtual total mass 40 with mass M. The force of gravity 42 acting on the total mass 40 effects a torque 46 on the C-arm 6 relative to the orbital axis 22 via the virtual lever arm 44 of the length L extending from the isocenter 24 to the overall center of gravity 38. The torque 46 in FIG. 1 is T=M·L. If the C-arm 6 is orbitally panned from the position shown in FIG. 1, the torque cosinusoidally decreases with the corresponding rotation angle since the force of gravity 42 no longer acts at a right angle to the lever arm 44.

Figure 2:
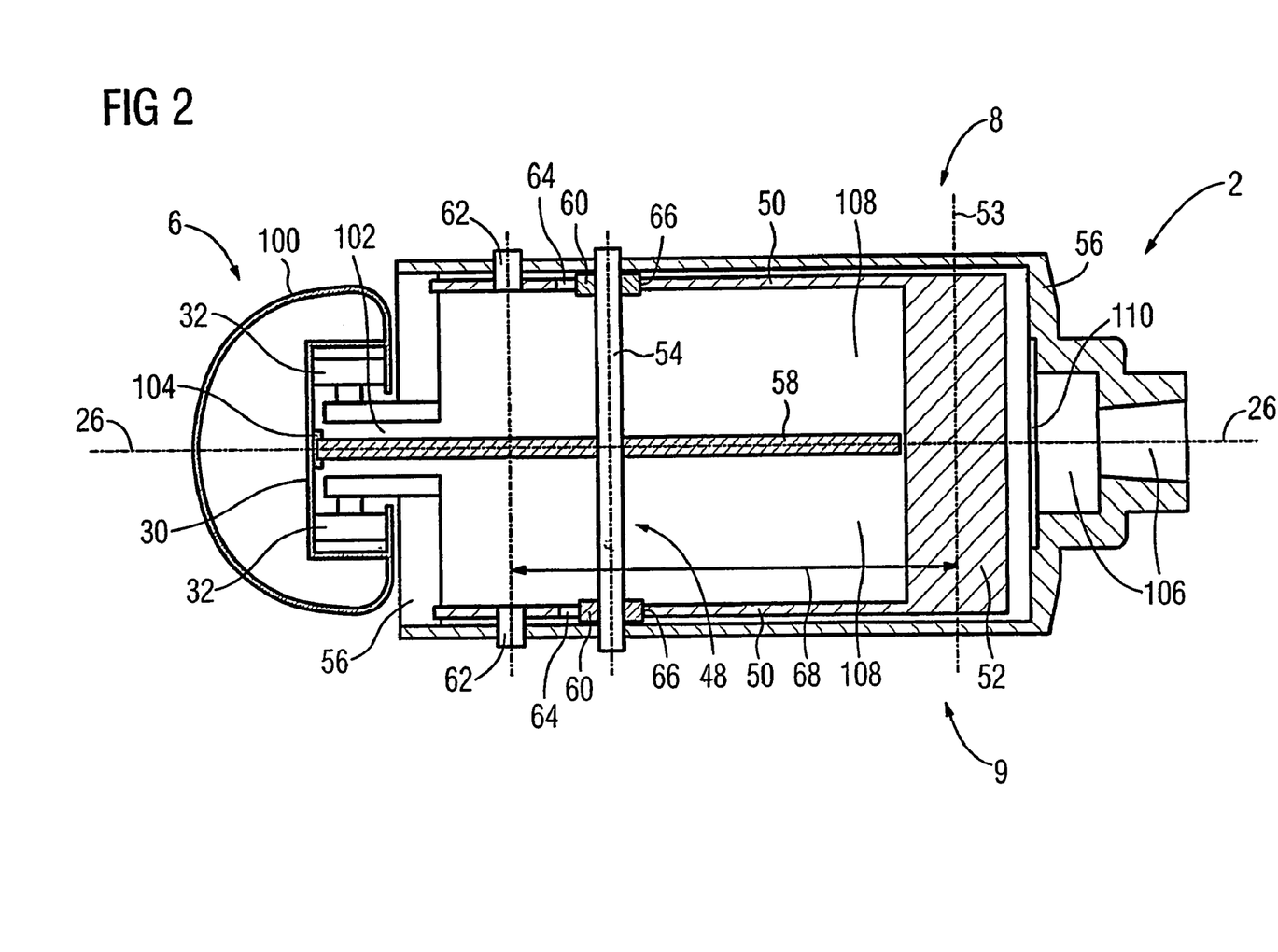
FIG. 2 is a section through the C-arm from FIG. 1 in the viewing direction of the arrow II.

A compensation device 9 is comprised in the support device 8 (see also FIG. 2 in this regard). The compensation device 9 has a gearwheel 48, two parallel extension arms 50 and a counterweight 52 connecting the extension arms 50 at the ends in a U-shape. The gearwheel 48 has a shaft 54 supported on the housing 56 of the support device 8, a crown gear 58 centrally attached on the shaft 54 and two pinions 60 attached near the shaft ends. The teeth (situated radially outwards) of the crown gear 58 engage teeth 104 permanently attached on the contact surface 30. The extension arms 50 with their ends situated opposite the counterweight 52 are fastened on shafts 62 parallel to the shaft 54 and orbital axis 22, which shafts 62 are supported on the housing 56 such that they can rotate. C-shaped recesses 64 are present near the shafts 62 and concentric to these. The radially outer edges of the recess 64 are provided with inner gearings 66 in which the pinions 60 engage. The counterweight 52 exhibiting the mass 2M is fastened on the free ends of the extension arms 50. The virtual lever arm 68 of the counterweight 52 amounts to L/2 relative to the shafts 62, such that via the force of gravity 74 this generates a torque 76 of T=2M·L/2=M·L which is equal in magnitude to the torque acting on the C-arm and exhibits the identical cosine dependency of the rotation angle.

By the movement coupling between teeth 104, crown gear 58, pinion 60, inner teeth 66 and extension arm 50, an orbital travel of the C-arm 6 in the direction 20 effects an orbital panning of the counterweight 52 around the shaft 62 in the direction of the arrow 69. The gearing is selected such that an angle change of the angle 28 effects the same (according to amount) angle change of the angle 70 between center longitudinal axis of the extension arms 50 and the perpendicular 72. Moreover, in FIG. 1 the gearing arrangement (thus the compensation device 9) is adjusted such that a 90° position of the angle 28 corresponds to a 90° position of the angle 70.

Without application of a counterforce, i.e., without the compensation device 9 coupled to the gearing 104, due to gravity the C-arm 6 would slide downwards in the direction of the arrow 49 into the support device 8 until the angle 28 is 0° and the overall center of gravity 38 finds a stable equilibrium position below the isocenter 24 in the direction of gravity.

Relative to the orbital axis 22, the compensation device generates the equal and opposite torque on the C-arm 6. The torque 76 is transferred to the gearwheel 48 via the inner teeth 66 and the pinion 60 and via this gearwheel 48 to the C-arm 6 via the teeth 104 of the contact surface 30 and thus counteracts the torque 46. In FIG. 1 the dimensions of the gear components are matched to one another such that this translation from torque 76 to torque 46 amounts to one to one. The two torques are equal and opposite and, in fact for each movement angle of the C-arm 6 cancel to zero on the orbital axis 22. The C-arm 6 is thus completely weight-compensated with regard to the orbital movement 20 and remains free of torque at every rotation position.

All components of the support device 8 and of the compensation device 9 of course have mass. If one excludes the counterweight 52 (strictly speaking together with the likewise movable extension arms 50 which also alter the center of gravity upon movement—for simplicity in the following only the counterweight 52 is discussed) from this consideration, support device 8 and compensation device 9 together have a virtual total mass 78 at the overall center of gravity 80. Since the support device 8 and compensation device 9 can be moved synchronously with the C-arm 6 around the angulation axis 26, the total mass 78 effects a torque around the angulation axis 26, the virtual lever arm 86 being the radial distance of the overall center of gravity 80 from the angulation axis 26.

FIG. 2 shows the C-arm apparatus 2 from FIG. 1 in the direction of the arrow II in the section at the level of the shaft 62. The C-arm 6 exhibits an approximately semi-circular hollow section cavity, whereby its wall 100 flattens on the side facing the support device 8 and is recessed in a central region 102. There the wall 100 is directed towards the inside of the C-arm 6 and forms the contact surface 30 on which the rollers 32 borne on the housing 56 run. The teeth 104 in which the teeth of the crown gear 58 engage are centrally affixed on the contact surface 30. The crown gear 58 is mounted in a fixed manner on the shaft 54 together with the pinions 60, whereby the shaft 54 is supported at one end in the housing 56 such that it can rotate. The extension arms 50 supporting the counterweight 52 are likewise supported in the housing 56 via the shafts 62 such that they can rotate. The inner gearing 66 on the recess 64 engages both pinions 60. In the housing 56 a receptacle 106 for rotatable bearing of the bearing axle 10 (not shown in FIG. 2) is provided at the end of the support device 8 situated opposite the C-arm 6.

The crown gear 58 runs approximately centrally in the housing 56, whereby the extension arms 50 and pinions 60 are situated near the inner border of the housing 56. Free spaces 108 thus arise for acceptance of additional components (not shown) of the C-arm apparatus 2 such as cable guides, drive motors or the like. The mechanically-stable connection between the extension arms 50 is achieved via the counterweight 52. A cover plate 110 seals the inner chamber of the housing 56 from the receptacle 106.

Figure 3:
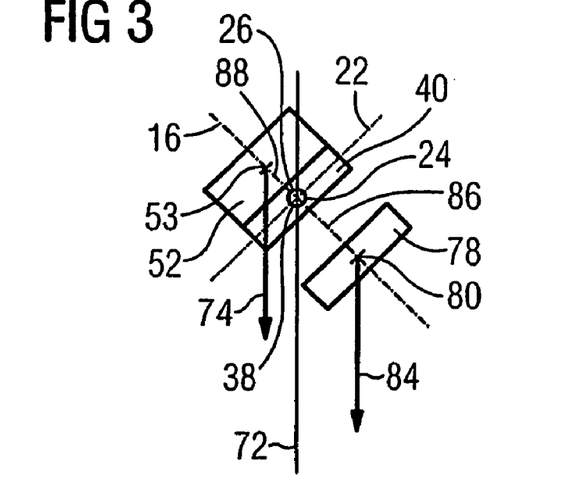
FIG. 3 is a mass model of the angularly-moved C-arm from FIG. 1.

FIG. 3 shows the plan view of the mass and lever ratios of the C-arm apparatus 2 from FIG. 1 in the direction of the arrow III. However, the C-arm in the shown 90° orbital position is additionally angularly tilted by approximately 45° relative to the perpendicular 72 in the counter-clockwise direction around the angulation axis 26.

FIG. 3 is a schematic drawing in which the entire arrangement of the counterweight 52 is shown as a single real component. All other real components of the C-arm 6 and of the x-ray system 4 are represented by their virtual total mass 40. All real components of the support device 8 and of the compensation device 9 with the exception of the counterweight 52 are represented by their virtual total mass 78.

Due to the angular tilting orbital axis 22 and central ray 16 are likewise tilted by approximately 45° relative to FIG. 1. The angulation axis 26 furthermore runs horizontal and perpendicularly penetrates the plane of the drawing in FIG. 2. Orbital axis 22, central ray 16 and angulation axis 26 furthermore intersect in the isocenter 24.

In the orbital 90° position of the C-arm 6, the total mass 40 with its overall center of gravity 38 lies on the angulation axis 26 and exerts no torque relative to this. Angular torques are generated only by the gravitational forces 84 and 74 acting on the total mass 78 and on the counterweight 52 with the lever arms 86 and 88 with regard to the angulation axis 26. The lever arm 88 is hereby the radial distance of the center of gravity 53 of the counterweight 52 from the angulation axis 26 (which, due to the 90° position (angle 70) of the counterweight here corresponds to the distance of the shaft 62 from the angulation axis 26). The lever arm 86 is the radial distance of the overall center of gravity 80 from the angulation axis 26.

For the following torque consideration, the cosine dependency of the torques on the angulation angle (which here is always the same for all considered values) is omitted for simplicity.

Due to the size of the total mass 78 of M/2 and the lever arm 86 of the length H, the total mass 78 effects a torque T=M/2·H=M·H/2. The lever arm 88 is therefore dimensioned at H/4. The counterweight 52 thus generates a torque T=2M·H/4=M·H/2 and compensates so the torque of the total mass 78 amounts to zero. All torques with regard to the angulation axis 26 are thus compensated and the C-arm apparatus 2 is also weight-compensated with regard to this axis. It remains free of forces at every arbitrary angulation position.

Figure 4:
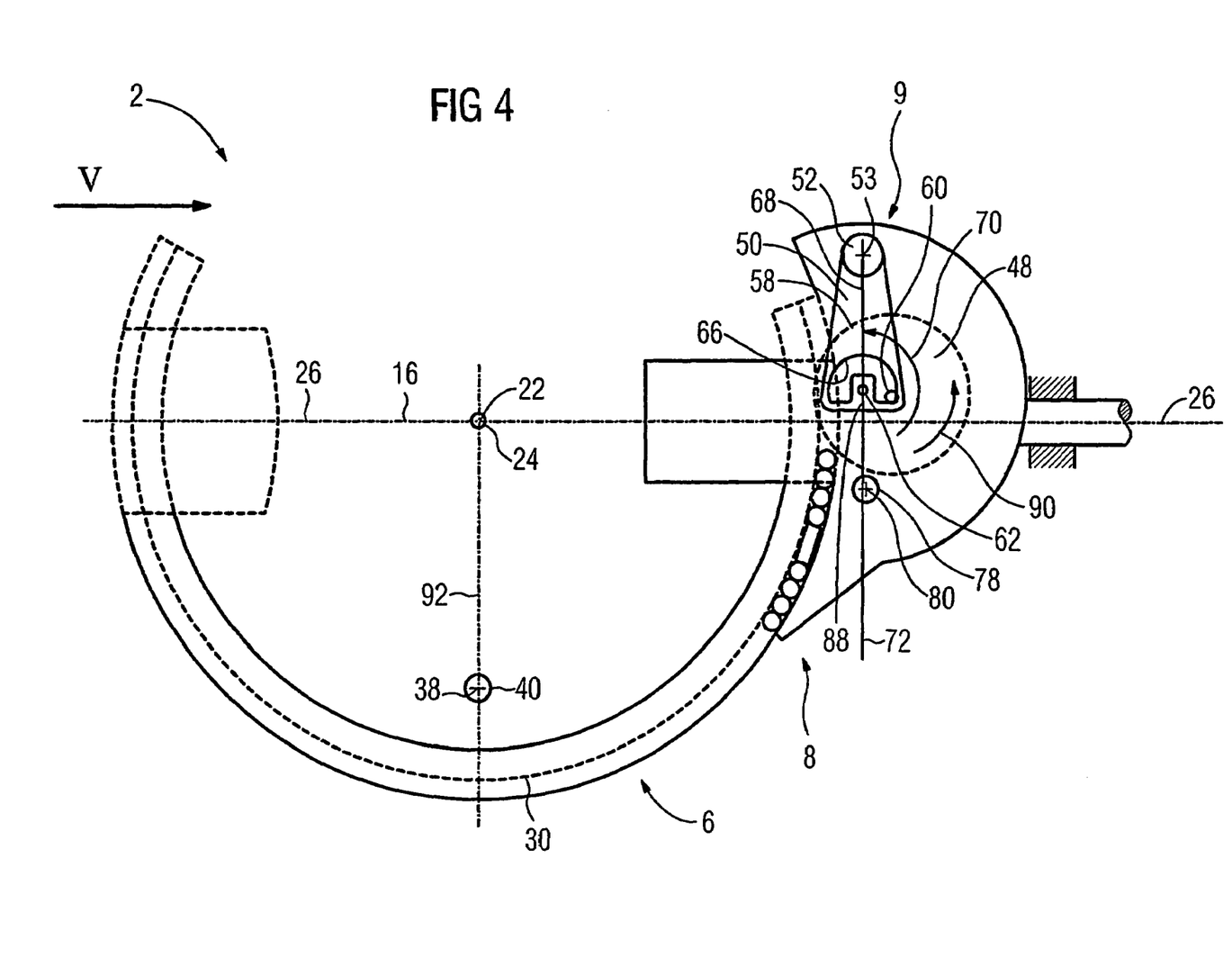
FIG. 4 shows the C-arm from FIG. 1 in 0° orbital position in a representation according to FIG. 1.

FIG. 4 shows the C-arm apparatus 2 from FIG. 1 with C-arm 6 panned downwards by 90°, thus in the 0° position. The central ray 16 then coincides with the angulation axis 26 so that the angle 28 amounts to 0°. The overall center of gravity 38 is located in the direction of gravity, thus vertically below the isocenter 24, which is why the C-arm 6 also assumes a stable equilibrium position without contrary torque. The compensation device 9 likewise exerts no torque on the C-arm 6. The counterweight 52 is namely located in an unstable equilibrium position relative to the shaft 62, meaning the angle 70 amounts to 180° relative to the perpendicular 72. The extension arms 50 are thus pivoted upwards by 90° relative to FIG. 1.

The extension arm 50 is for the most part executed massively and possesses a not-insignificant weight which is likewise to be taken into account as a compensation mass for the weight compensation. Strictly speaking, as already mentioned above the extension arm 50 thus counts towards the total weight 52 given weight considerations. The remaining gearing arrangement parts are designed such that the position of the overall center of gravity 80 does not change in relation to FIG. 1 given their movement since the counterweight 52 (together with the extension arm 50) is itself excluded from this consideration.

Given movement of the C-arm 6 from the position according to FIG. 1 into the position according to FIG. 4, the C-arm 6 performs a 90° pan. Due to the engagement of the gearing 104 in the crown gear 58, the gearwheel 48 hereby performs approximately one and a half rotations in the direction of the arrow 90 due to the gearing arrangement ratio between the two effective radii of the gearings (radial distance of the gearing 104 from the orbital axis 22 at the diameter of the crown gear 58). The pinion 60 passes through the same angle change as the crown gear 58. Due to the interaction of the pinion 60 with the inner gearing 66 and the gear reduction associated with this (diameter of the pinion 60 at radial distance of the inner gearing 66 from the shaft 62), the extension arm 50 passes through the same 90° angle change as the C-arm 6, meaning that the overall gearing arrangement ratio of the gearing arrangement is 1:1. At arbitrary intermediate positions between FIG. 3 and FIG. 4, the cosine dependencies of the torques generated by the total mass 40 and the counterweight 52 are therefore equal, which is why the C-arm 6 is weight-compensated at every arbitrary orbital angle position, even beyond those cases shown in Figures.

Figure 5:
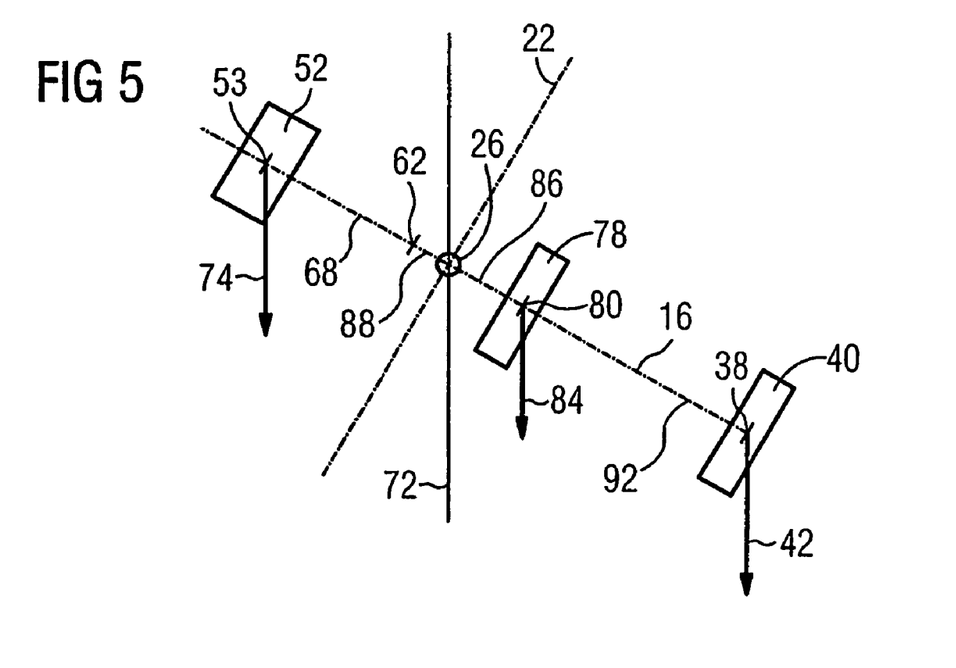
FIG. 5 is a mass model of the angularly-moved C-arm from FIG. 4 in a representation according to FIG. 3.

FIG. 5 shows the C-arm apparatus 2 from FIG. 3 in the 0° orbital position in the direction of the arrow V, but angularly tilted by approximately 60° in the counter-clockwise direction in contrast to FIG. 3. As in FIG. 3 (with the exception of the counterweight 52), again only the virtual total masses 40 and 78 of the arrangement are shown. The total mass 78 with unchanged distance relative to the angulation axis 26 hereby again generates the same torque T=M/2·H=M·H/2 with the omission of the cosine dependencies. Since the center of gravity 38 now no longer lies on the angulation axis 26, an additional torque with lever arm 92 also arises relative to the angulation axis 26 due to the total mass 40. The lever arm 92 corresponds to the radial distance of the center of gravity 38 from the angulation axis 26, which in the shown example corresponds to equal to the lever arm 44 from FIG. 1. The additional torque T=M·L herewith arises. T=M·H/2+M·L thus acts relative to the angulation axis 26 due to the masses 78 and 40.

Since the counterweight 52 is now moved on its extension arm 50, its lever arm now amounts (relative to the angulation axis 26) to the sum of the distance 88 of the shaft 62 from the angulation axis 26 and the lever arm 68, namely the distance of the counterweight 52 from the shaft 62. The contrary torque due to the counterweight 52 is accordingly T=2M·(H/4+L/2)=M·H/2+M·L, which precisely corresponds to the sum of the other two torques.

Due to the mass and length ratios in the C-arm apparatus 2, this is thus completely weight-compensated in every orbital and angular position.

Figure 6:
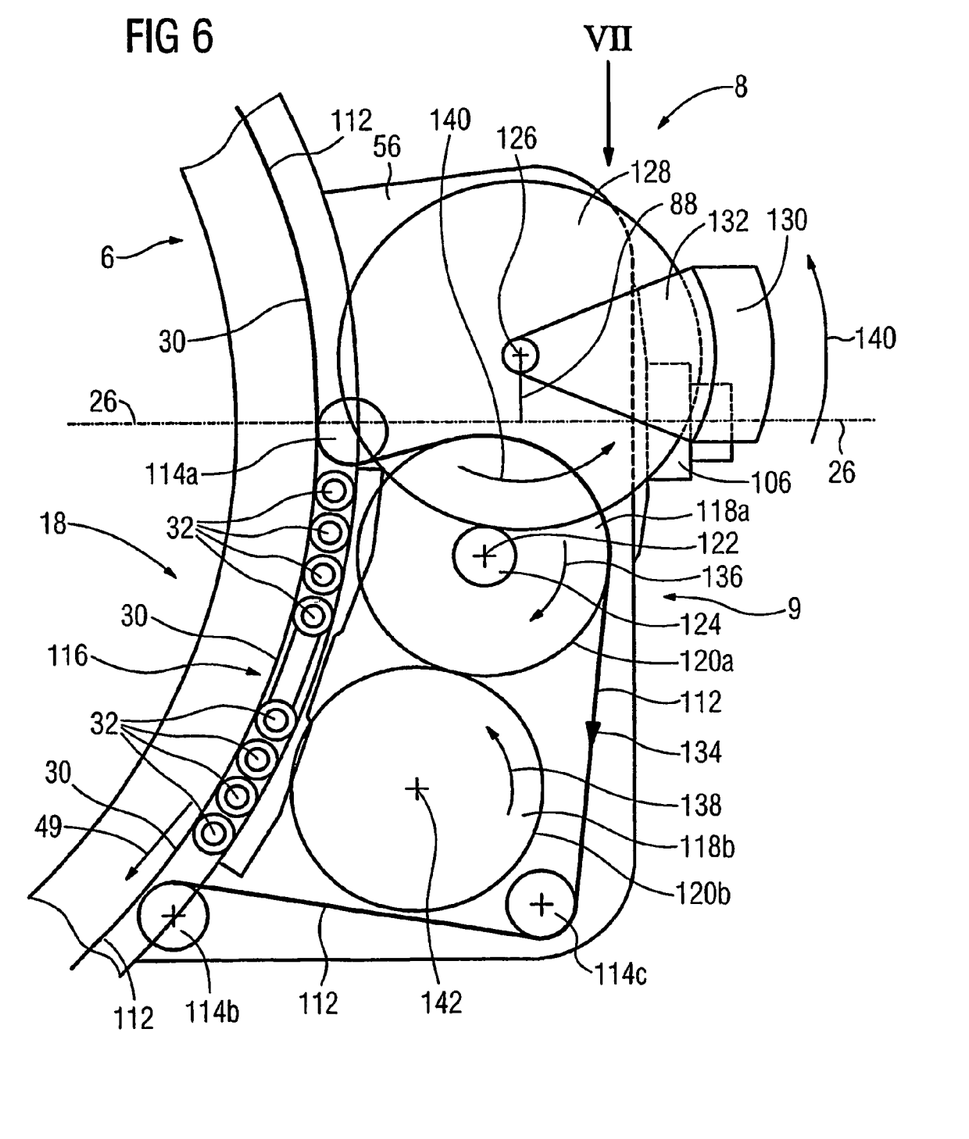
FIG. 6 shows an alternative embodiment of a support device with a compensation device in a representation according to FIG. 1.

FIG. 6 shows an alternative embodiment for the bearing device 8 with compensation device 9. Instead of the teeth 104, a toothed belt 112 is directed on the contact surface 30 of the C-arm 6. This toothed belt 112 is permanently connected with the C-arm 6 at the end of the C-arm 6 that is not visible in FIG. 6 and lies on the contact surface 30 on nearly the entire C-arm length. Only in a region 116 situated between deflection rollers 114a and 114b is the toothed belt 112 directed away from the contact surface 30. It runs from the deflection roller 114a over a cable drum 118a and a deflection roller 114c back to the deflection roller 114b on the C-arm 6. The cable drum 118a comprises a circumferential-side gearing 120a in which the toothed belt 112 engages. Two pinions 124 are attached near the shaft ends on a shaft 122 passing through the cable drum 118a and borne on the housing 56. These pinions 124 respectively engage in the gearing of two crown gears 128 born on a shaft 126 near the shaft ends. Another extension arm 132 that supports a counterweight 130 on its free end is attached at one end to the shaft 126.

Feed lines (not shown) are wound on the cable drums 118b, which feed lines lead from the cable drum 118a along the C-arm 6 to the image intensifier 14 (not visible in FIG. 6) and from the cable drum 118*b* to the x-ray source 12 (not visible).

Given an orbital travel of the C-arm 6 on the support device 8 in the direction of the arrow 49, the toothed belt 112 is directed over the roller arrangement described above in the direction of the arrow 134 and hereby displaces the cable drum 118*a* into rotation in the direction of the arrow 136. The cable drum 119*a* winds the feed cable approaching from the image intensifier 14 in the direction 49. The roller 118*a* displaces the cable drum 118 into rotation in the direction 138, which in turn unwinds the feed cable (not shown) and releases it in the direction 49 of the x-ray source 12. Simultaneously with the cable drum 118*b*, the cable drum 118*a* displaces the gearwheel 128 into motion in the direction 140 via the pinion 124. The extension arm 132 and the counterweight 130 are hereby simultaneously panned around the axis 126.

The dimensioning of the mass and lever ratios is executed corresponding to the embodiment according to FIG. 1 through FIG. 5. Merely altered values of total mass 78 and position of the center of gravity 80 (and therewith of the lever arm 86) of the support device 8 and compensation device 9 would lead to a different measurement for the lever arm 88, thus to a different placement of the shaft 62. The gearing arrangement ratio of the individual gear speeds is again tuned such that an angle change given orbital travel of the C-arm 6 effects the same angle change of the counterweight 130. The moment ratios in FIG. 6 thus correspond to those in FIG. 1. The mass of the counterweight 52 of 2M is merely split up into two partial masses of M each of the two counterweights 130.

Figure 7:
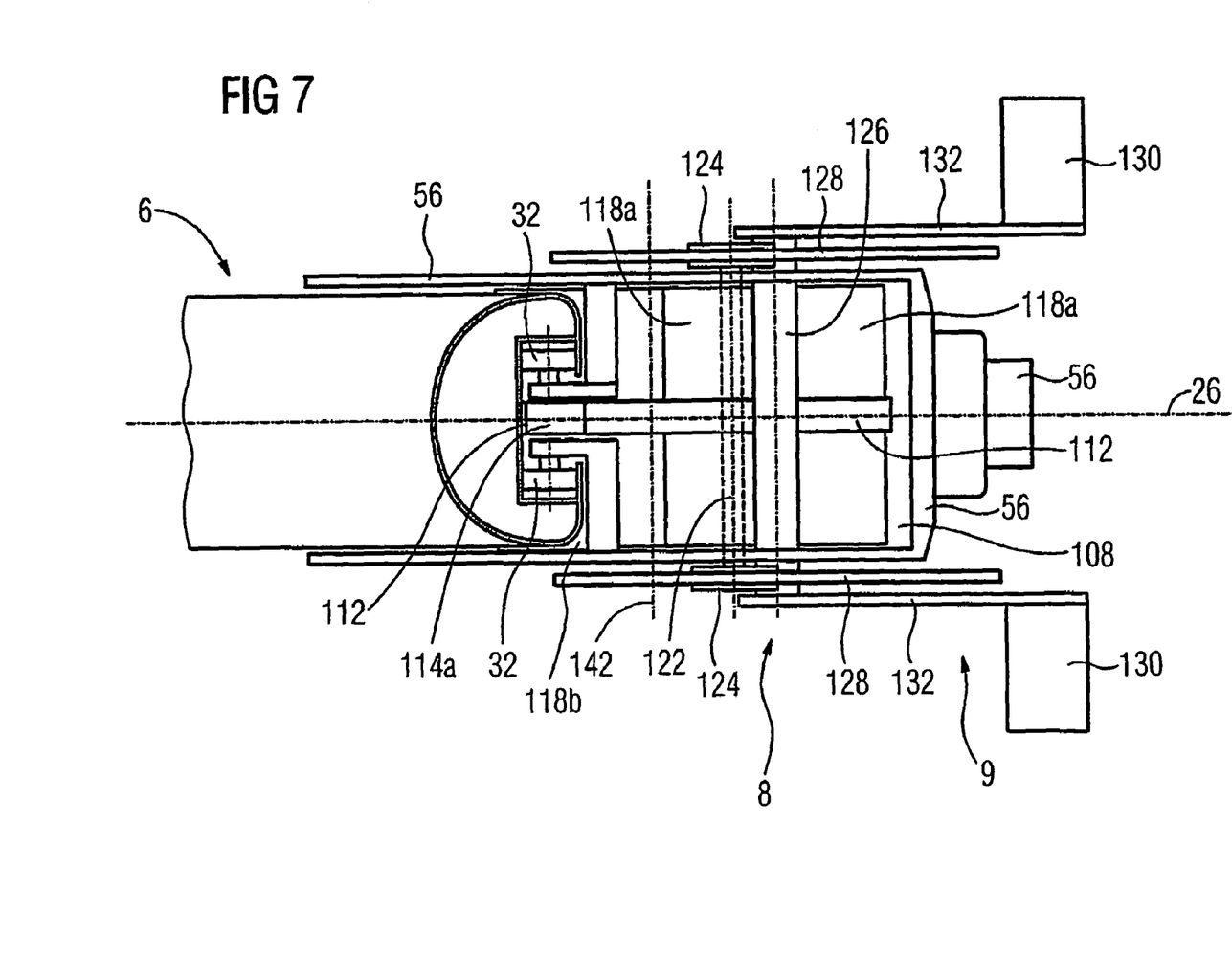
FIG. 7 is a section through the device from FIG. 6 in the viewing direction of the arrow VII.

FIG. 7 shows the arrangement from FIG. 6 in the viewing direction of the arrow VII in the section above the shaft 126. In contrast to the exemplary embodiment according to FIG. 5, essentially the cable drums 118*a* and 118*b* are located in the inside 108 of the bearing device 8. The pinions 124 connected with the cable drum 118*a* are mounted on both sides outside of the bearing device 8, as well as the gearwheels 128, extension arms 132 and counterweights 130. The synchronous movement of the counterweights 130 is ensured via the rigid connection through the axis 126. A disadvantage of the embodiment according to FIG. 1 through FIG. 5 is that the feed lines (not shown) running in part in the surroundings of the C-arm apparatus 2 interfere and are accident-prone since these easily get caught or twist. Instead of panning outside on the C-arm apparatus 2, the counterweights 130 in the embodiment according to FIG. 6 and FIG. 7 are significantly less disruptive and can, if applicable, be housed in an additional housing (not shown) entirely surrounding the compensation device 9, whereby a C-arm apparatus 2 entirely closed from the outside results in turn.

Although modifications and changes may be suggested by those skilled in the art, it is the invention of the inventor to embody within the patent warranted heron all changes and modifications as reasonably and properly come within the scope of his contribution to the art.

I claim:

1. An x-ray C-arm apparatus comprising:
   a C-arm exhibiting a C-arm plane;
   a plurality of components mounted on said C-arm, including an x-ray source and a radiation detector;
   a C-arm mount to which said C-arm is mounted for rotation around an orbital axis, said C-arm and said plurality of components mounted thereon having an overall center of gravity, and said plurality of components mounted on said C-arm, in combination exerting a first torque on said C-arm totaling all respective torques produced by said plurality of components; and
   a compensation device located on said C-arm entirely between said x-ray source and said radiation detector, said compensation device comprising a counterweight mounted on a rotatable arm that spaces said counterweight from said C-arm, and a gear arrangement that interacts with said C-arm upon rotation of said C-arm to rotate said rotatable arm and said counterweight, dependent on rotation of said C-arm to produce a second torque that at least partially compensates said first torque.

2. An x-ray C-arm apparatus as claimed in claim 1 wherein said counterweight is mounted for rotation around a rotational axis and wherein said gearing arrangement, when said C-arm exhibits an angular change, having an absolute angular magnitude, around said orbital axis, causes said counterweight to rotate through the same absolute angular magnitude around said rotational axis.

3. An x-ray C-arm apparatus as claimed in claim 2 wherein said counterweight is movable in said orbital plane of said C-arm.

4. An x-ray C-arm apparatus as claimed in claim 2 wherein said C-arm mount allows movement of said C-arm around an angulation axis that intersects said orbital axis at a right angle.

5. An x-ray C-arm apparatus as claimed in claim 2 comprising a support device having a housing containing said C-arm mount and said compensation device.

6. An x-ray C-arm apparatus as claimed in claim 5 wherein said gearing arrangement is a multi-stage geared transmission mounted on said support device, said transmission comprising components disposed parallel to said orbital plane, and said transmission producing a translation of 1:1 between said center of gravity and said counterweight.

7. An x-ray C-arm apparatus as claimed in claim 6 wherein one of said components of said transmission is an extension arm having an end at which said counterweight is mounted, and comprising an interior having gearing therein.

8. An x-ray C-arm apparatus as claimed in claim 2 wherein said counterweight is movable in said orbital plane of said C-arm and wherein said transmission and said counterweight form a cavity containing a cable drum on which a feed cable for moving said C-arm around said orbital axis is wound.1

* * * * *